United States Patent [19]
Inukai et al.

[11] Patent Number: 5,921,936
[45] Date of Patent: Jul. 13, 1999

[54] SYSTEM AND METHOD FOR EVALUATING THE CIRCULATORY SYSTEM OF A LIVING SUBJECT

[75] Inventors: Hidekatsu Inukai, Nagoya; Hiroshi Sakai, deceased, late of Komaki, both of Japan, by Hiroko Sakai, heir

[73] Assignee: Colin Corporation, Komaki, Japan

[21] Appl. No.: 08/867,814

[22] Filed: Jun. 3, 1997

[51] Int. Cl.⁶ ................................................... A61N 5/00
[52] U.S. Cl. ......................... 600/490; 600/500; 600/485
[58] Field of Search .................... 600/490, 485, 600/493, 494, 495, 496, 500, 504

[56] References Cited

U.S. PATENT DOCUMENTS

| | | | |
|---|---|---|---|
| 4,432,373 | 2/1984 | Ogawa et al. | 600/493 |
| 4,458,690 | 7/1984 | O'Conner et al. | 600/493 |
| 4,649,929 | 3/1987 | Weaver et al. | |
| 4,677,984 | 7/1987 | Sramek | 600/429 |
| 5,033,472 | 7/1991 | Sato et al. | |
| 5,054,494 | 10/1991 | Lazzaro et al. | 600/490 |
| 5,103,831 | 4/1992 | Niwa | 600/500 |
| 5,237,997 | 8/1993 | Greubel et al. | 600/500 |
| 5,243,990 | 9/1993 | Aung et al. | 600/490 |
| 5,291,895 | 3/1994 | McIntyre | 600/490 |
| 5,564,427 | 10/1996 | Aso et al. | 600/500 |
| 5,603,329 | 2/1997 | Hosaka et al. | 600/500 |
| 5,671,750 | 9/1997 | Shindoa | 600/493 |
| 5,743,856 | 4/1998 | Oka et al. | 600/485 |
| 5,752,920 | 5/1998 | Ogura et al. | 600/485 |

FOREIGN PATENT DOCUMENTS

| | | |
|---|---|---|
| 0-204-394 | 12/1986 | European Pat. Off. . |
| 0-534-022-A1 | 3/1993 | European Pat. Off. . |
| 0-772-998-A2 | 5/1997 | European Pat. Off. . |
| A-6-292660 | 10/1994 | Japan . |

*Primary Examiner*—Robert L. Nasser
*Assistant Examiner*—Michael Astorino
*Attorney, Agent, or Firm*—Oliff & Berridge, PLC

[57] ABSTRACT

A system that accurately evaluates a living subject's circulatory system, even if the living subject is taking high blood pressure medication includes a time-difference determining device that determines a time difference between predetermined periodic points on a subject's electrocardiographic waveform and predetermined periodic points on corresponding oscillatory pressure-pulse waves of the living subject. A strain application device applies a physical strain to the subject's body for a predetermined period of time so that the subject' blood pressure changes. A blood-pressure measurement device measures the subject's blood pressure while the subject's blood pressure is changing. A circulatory-system evaluation device determines a relationship between changes in the subject's blood pressure and corresponding time differences determined by the time-difference determining. The circulatory-system evaluation device evaluates the subject's circulatory system based on the hysteresis present in the relationship.

40 Claims, 12 Drawing Sheets

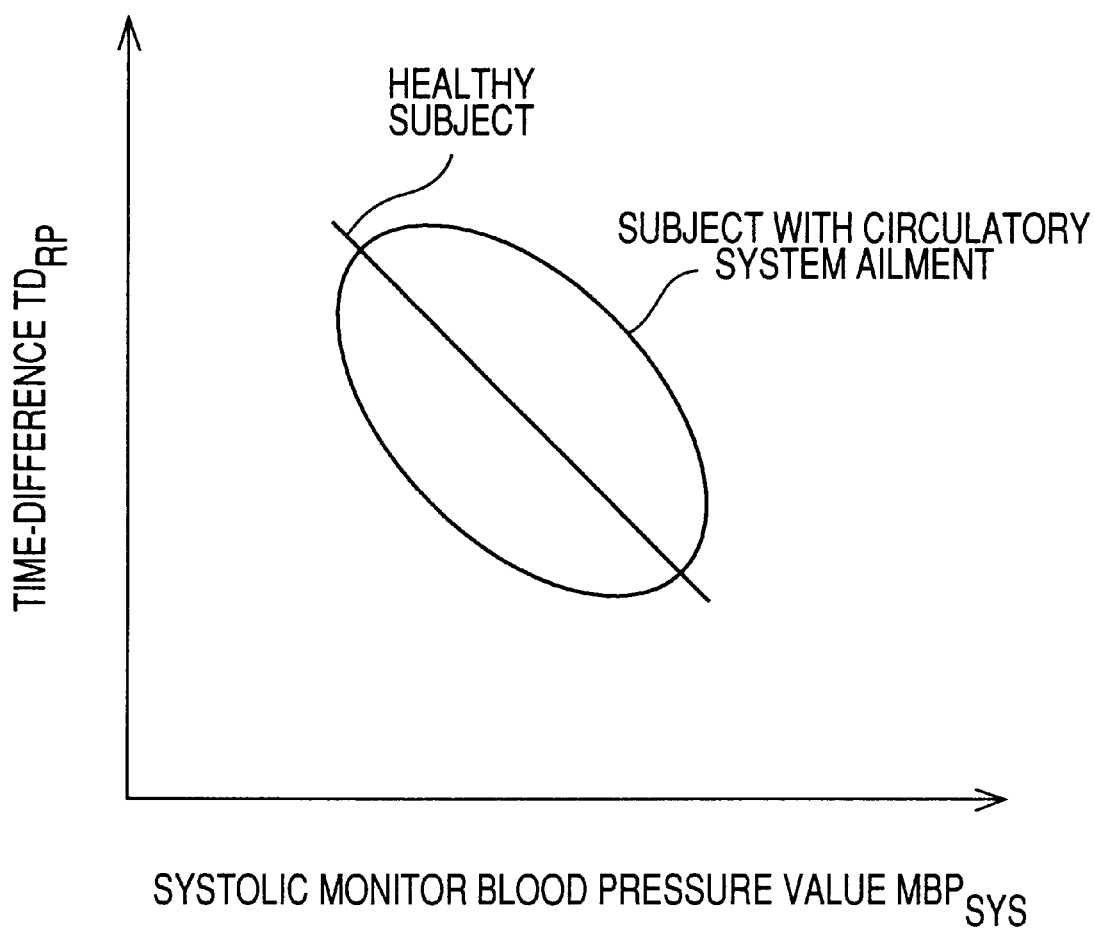

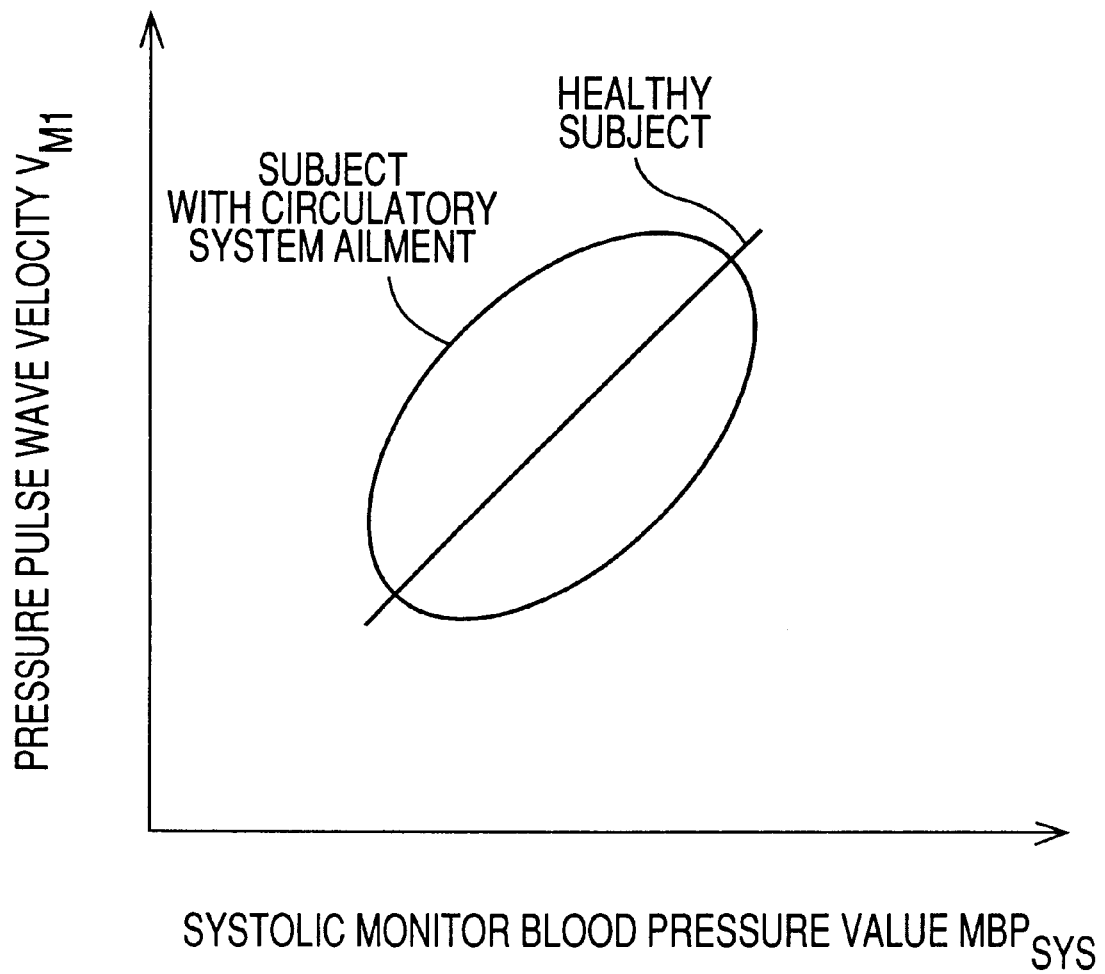

SYSTEM AND METHOD FOR EVALUATING THE CIRCULATORY SYSTEM OF A LIVING SUBJECT

BACKGROUND OF THE INVENTION

1. Field of Invention

This invention relates to medical diagnostic devices. More specifically, this invention is directed to a system and method for evaluating the circulatory system of a living subject.

2. Description of Related Art

Some circulatory ailments that cause high blood pressure, such as arteriosclerosis, are discovered by measuring the subject's blood pressure with a blood pressure measurement apparatus. One such blood pressure measurement apparatus is disclosed in Japanese Laid-Open Application No. 6-292660.

The blood-pressure measurement device measures the blood pressure of a living subject using a cuff that is wrapped around a portion of the living subject. The cuff applies pressure to the living subject. The living subject's blood pressure is measured using a well-known oscillometric method, which is based on detecting changes in the amplitude of a synchronous wave pulsation as the pressure applied by the cuff is gradually released.

Although a blood pressure measurement is effective in discovering the existence of high blood pressure in a living subject, it is not an effective method for evaluating improvement in the underlying cause of the living subject's high blood pressure brought about by dietary treatments. Blood pressure measurement is not effective in evaluating the effects of dietary treatment on the circulatory ailment because high-blood-pressure patients typically take blood-pressure-reducing medication. Thus, because the living subject's blood pressure is kept at normal levels by medication, a blood pressure measurement will not reveal if the underlying condition causing the living subject's high blood pressure is improving.

SUMMARY OF THE INVENTION

This invention provides a device that accurately evaluates a living subject's circulatory system, even if the living subject is taking high-blood-pressure medication. The device provides a time-difference determining device that determines a time difference between predetermined periodic points on a subject's electrocardiographic waveform and predetermined periodic points on corresponding oscillatory pressure-pulse waves of the living subject. A strain application device applies a physical strain to the subject's body for a predetermined period of time so that the subject's blood pressure changes. A blood-pressure measurement device measures the subject's blood pressure while the subject's blood pressure is changing. A circulatory-system evaluation device determines a relationship between changes in the subject's blood pressure and corresponding time differences determined by the time-difference determining device. The circulatory-system evaluation device evaluates the subject's circulatory system based on the hysteresis present in the determined relationship.

The inventors have discovered, as a result of extended study, that the relationship between changes in a subject's blood pressure and changes in the corresponding time differences between predetermined periodic points on the subject's electrocardiographic waveform and predetermined periodic points on corresponding oscillatory pressure-pulse waves of the living subject exhibits little or no hysteresis if the subject's circulatory system is healthy. Furthermore, the relationship exhibits hysteresis if the subject's circulatory system is not healthy.

In a preferred embodiment, a propagation velocity determining device is used to determine the propagation velocities of a subject's oscillatory pressure-pulse waves based on the time difference determination by the time-difference determining device. In this embodiment, the circulatory-system evaluation device determines a relationship between changes in the subject's blood pressure and changes in the propagation velocities of corresponding oscillatory pressure-pulse waves. The circulatory-system evaluation device evaluates the subject's circulatory system based on the hysteresis present in the determined relationship. The amount of hysteresis present is an indicator of the relative health of the subject's circulatory system.

These and other features and advantages are described in or are apparent from the following detailed description of the preferred embodiments.

BRIEF DESCRIPTION OF THE DRAWINGS

The preferred embodiments of this invention will be described in detail, with reference to the following Fig.s, wherein:

FIG. 6 is a relationship determined by the circulatory-system evaluation device of FIGS. 1 and 3;

FIG. 10 shows a relationship determined by the circulatory-system evaluation device of FIGS. 1 and 8.

DETAILED DESCRIPTION OF PREFERRED EMBODIMENTS

Figure 1:
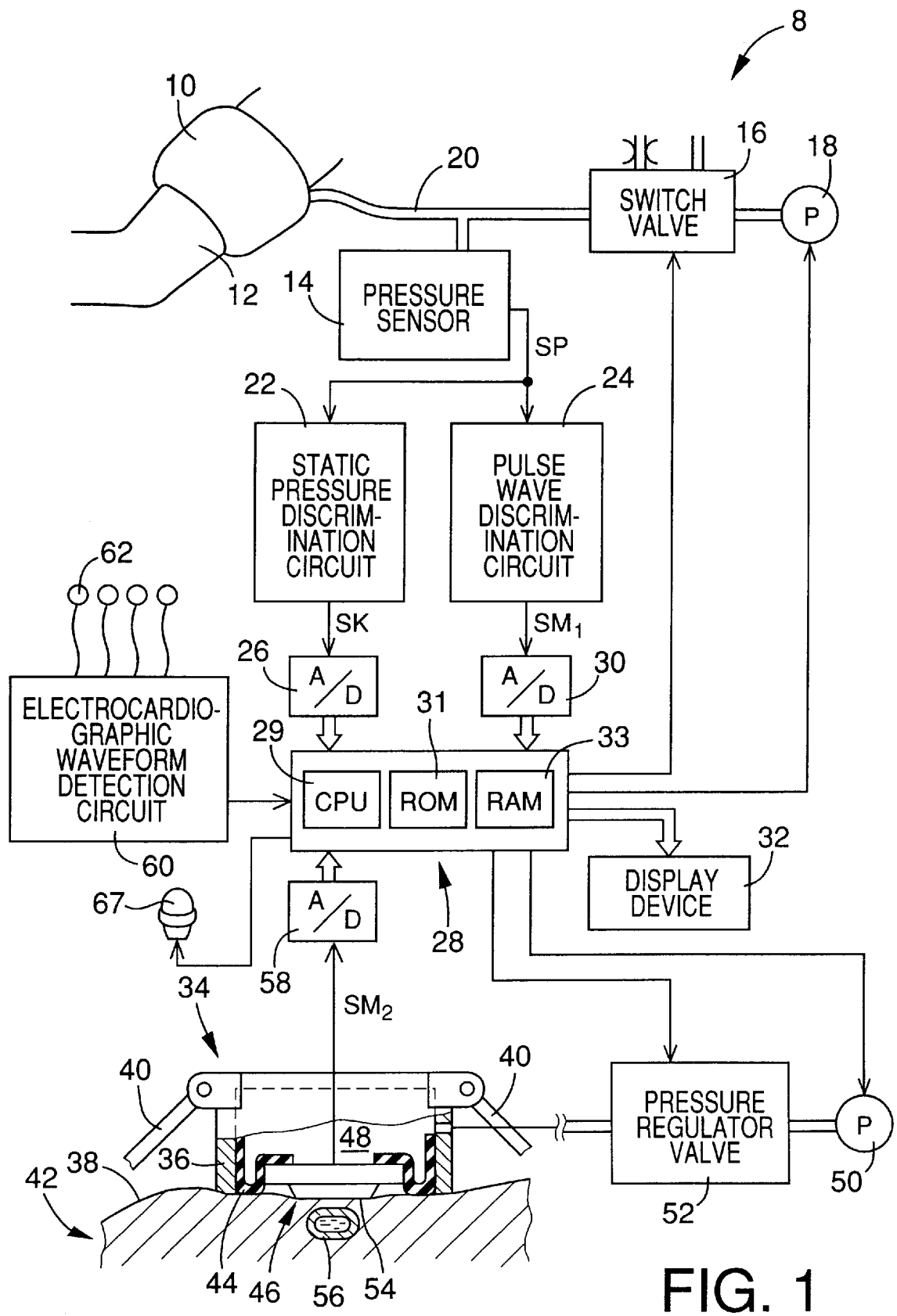
FIG. 1 is a combined schematic and block diagram of the circulatory-system evaluation device of this invention.

FIG. 1 shows the circulatory-system evaluation device 8 of this invention. The device 8 comprises an inflatable cuff 10 which is preferably formed by a rubber bag that is positioned inside a flexible cloth bag. The inflatable cuff 10 is wrappable around a portion of a living subject, e.g., an upper arm 12 of a subject.

The inflatable cuff 10 is connected via piping 20 to a pressure sensor 14, a switch valve 16 and a first air pump 18.

The switch valve 16 is selectively placeable in either an inflation position, a slow-deflation position or a quick-deflation position. In the inflation position, the switch valve 16 allows pressurized air from the first air pump 18 to be supplied to the inflatable cuff 10. In the slow-deflation position, the switch valve 16 allows the pressurized air in the inflatable cuff 10 to be slowly discharged. In the quick-deflation position, the switch valve 16 allows the pressurized air in the inflatable cuff 10 to be quickly discharged.

The pressure sensor 14 detects an air pressure in the inflatable cuff 10 and supplies a pressure signal SP, representing the detected pressure, to a static-pressure discrimination circuit 22 and a pressure-pulse-wave discrimination circuit 24. The static-pressure discrimination circuit 22 includes a low-pass filter that extracts a static component contained in the pressure signal SP, i.e., a cuff pressure signal SK that represents the static cuff pressure. The cuff pressure signal SK is supplied to an electronic control device 28 via a first A/D converter 26.

The pressure-pulse-wave discrimination circuit 24 includes a band-pass filter that extracts an oscillatory component of the pressure signal SP falling within a predetermined frequency range. The oscillatory component is supplied as a cuff pressure signal $SM_1$ to the electronic control device 28 via a second A/D converter 30. The cuff pressure signal $SM_1$ represents an oscillatory pressure wave that is produced from a brachial artery of the subject and that propagates to the area on the subject's right arm 12 in contact with the inflatable cuff 10.

The electronic control device 28 preferably includes a central processing unit (CPU) 29, a read-only memory (ROM) 31, a random-access memory (RAM) 33 and an input-output (I/O) port (not shown). The CPU 29 processes input signals according to control programs pre-stored in the ROM 31 using the RAM 33 as temporary storage. In addition, the CPU 29 outputs display signals to a display device 32.

When a measurement is initiated, the CPU 29 supplies a control signal to the switch valve 16 to place it in the inflation position and a drive signal to the first air pump 18 to inflate the inflatable cuff 10, thus compressing the upper portion of the subject's right arm 12. The CPU 29 then supplies a control signal to the switch valve 16 to place it in the slow-deflation position, thus gradually reducing the air pressure in the inflatable cuff 10.

While the air pressure in the inflatable cuff 10 is gradually reduced, the CPU 29 obtains the cuff pressure signal $SM_1$ and the cuff pressure signal SK from the pressure sensor 14 via the pressure-pulse-wave discrimination circuit 24 and the static-pressure discrimination circuit 22, respectively. The CPU 29 then determines the subject's systolic blood pressure value SBP, the subject's diastolic blood pressure value DBP and the subject's mean blood pressure value BP based on the obtained signals $SM_1$ and SK using well-known oscillometric blood pressure measuring techniques. These techniques are based on the variation of the amplitudes of the heartbeat-synchronous pulses of the oscillatory pressure-pulse wave (i.e., the cuff pressure pulse signal $SM_1$).

The circulatory-system evaluation device 8 further includes a oscillatory pressure-pulse-wave detection probe 34. The oscillatory pressure-pulse-wave detection probe 34 has a container-like housing 36 that is detachably worn, using attachment bands 40, on a body surface 38 of a subject's wrist 42 downstream of an upper arm. The oscillatory pressure-pulse-wave detection probe 34 is preferably worn on the other than the arm 12 around which the inflatable cuff 10 is worn. However, the oscillatory pressure-pulse-wave detection probe 34 may also be worn downstream of the upper arm 12 around which the inflatable cuff 10 is worn.

The oscillatory pressure-pulse-wave detection probe 34 is positioned on the subject's wrist 42 such that an opening of the housing 36 is opposed to the body surface 38. A pressure-pulse-wave sensor 46 is supported by the housing 36 via a diaphragm 44 such that the pressure-pulse-wave sensor 46 is movable relative to the housing 36 and is advanceable through the opening of the housing 36.

The housing 36, the diaphragm 44 and the pressure-pulse-wave sensor 46 cooperate with one another to define a pressure chamber 48. Pressurized air is supplied to the pressure chamber 48 from a second air pump 50 via a pressure regulator valve 52. Thus, the pressure-pulse-wave sensor 46 is pressed against a radial artery 56 of the subject via the body surface or skin 38 with a pressing force $P_{HD}$. The pressing force $P_{HD}$ corresponds to the air pressure in the pressure chamber 48.

The pressure-pulse-wave sensor 46 includes a number of semiconductor pressure-sensing elements (not shown) which are arranged along a pressing surface 54 of a semiconductor chip. The semiconductor chip is suitably formed from monocrystalline silicon.

The pressure-pulse-wave sensor 46 is pressed against the subject's radial artery 56 via the body surface 38 of the subject's wrist 42 to detect oscillatory pressure-pulse waves of the subject. The oscillatory pressure-pulse waves are produced by the subject's cardiac muscle and propagate along the radial artery 56. They are transmitted to the pressure-pulse-wave sensor 46 via the body surface 38. The pressure-pulse-wave sensor 46 generates an oscillatory pressure-pulse-wave signal $SM_2$ representing the detected oscillatory pressure-pulse wave. The oscillatory pressure-pulse-wave signal $SM_2$ is input to the electronic control device 28 via a third A/D converter 58. Thus, the pressure-pulse-wave sensor 46 detects an oscillatory pressure-pulse wave propagating through the subject's radial artery 56.

The CPU 29 of the electronic control device 28 supplies drive signals to the second air pump 50 and control signals to the pressure regulator valve 52 to regulate the air pressure in the pressure chamber 48. By regulating the air pressure in the pressure chamber 48, the CPU 29 regulates the magnitude of the pressing force $P_{HD}$ applied by the pressure-pulse-wave sensor 46 to the subject's radial artery 56 via the body surface 38.

The CPU 29 determines an optimum value for the pressing force $P_{HD}$ for the pressure-pulse-wave sensor 46 based on the respective magnitudes of heartbeat-synchronous pulses of the oscillatory pressure-pulse wave detected by the pressure-pulse-wave sensor 46 while the air pressure of the chamber 48 is changed. The CPU 29 then controls the pressure regulator valve 52 to maintain the optimum pressing force $P_{HD}$.

The circulatory-system evaluation device 8 also includes an electrocardiographic-waveform detection circuit 60. The electrocardiographic-waveform detection circuit 60 continuously detects an electrocardiographic waveform that indicates the change in electric potential of the subject's cardiac muscle. The electrocardiographic-waveform detection circuit 60 determines the electrocardiographic waveform from signals supplied by multiple electrodes 62. The electrodes 62 are placed at predetermined positions on the subject. The electrocardiographic-waveform detection circuit 60 is suitably an electrocardiograph, and the electrocardiographic waveform is suitably an electrocardiogram detected by the electrocardiograph.

The electrocardiographic-waveform detection circuit 60 supplies the electrocardiographic waveform to the electronic control device 28. The display device 32 may optionally record the electrocardiographic waveform on a recording sheet (not shown).

The circulatory-system evaluation device 8 also includes an indicator lamp 67. The indicator lamp 67 is used to signal the living subject being evaluated to begin a strain operation, as is described in more detail below.

Figure 2:
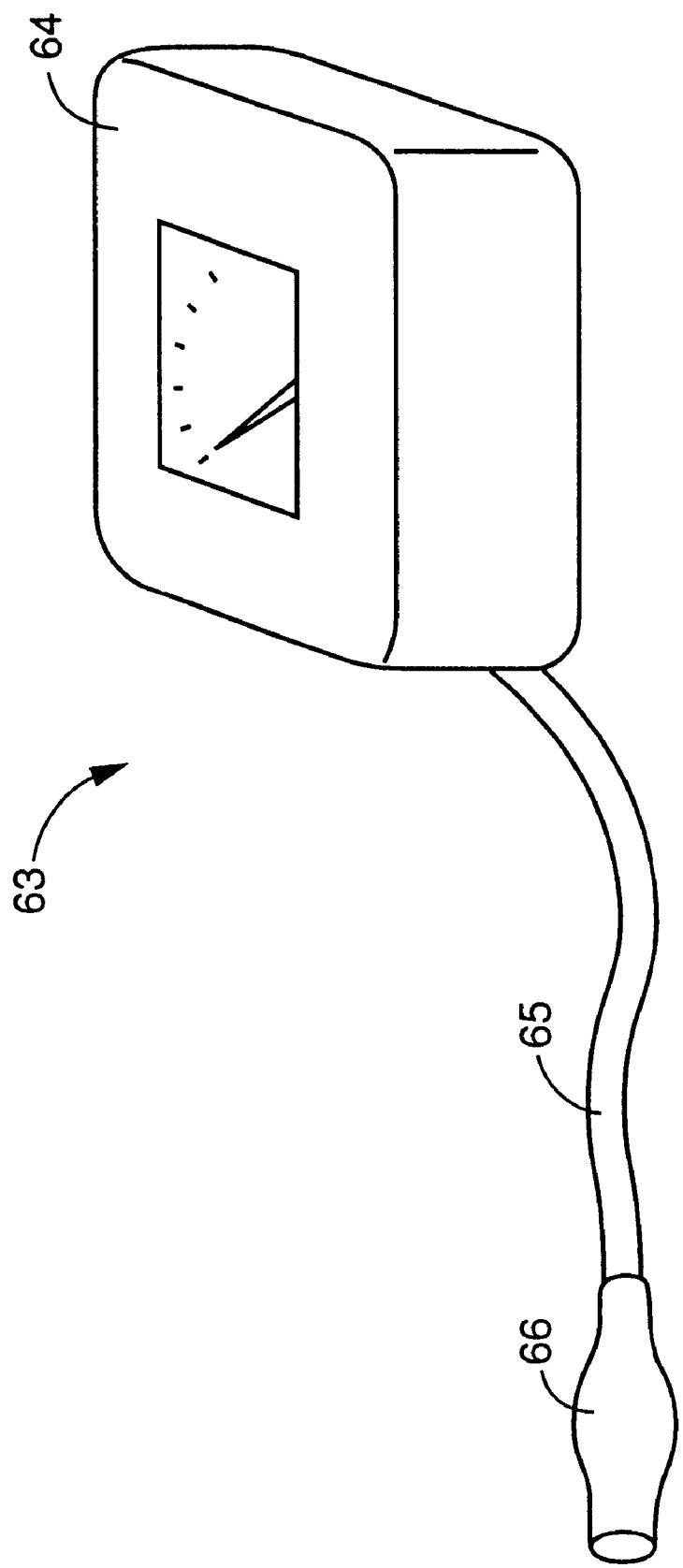
FIG. 2 is a perspective view of a thoracic-cavity pressure applicator and measurement device used in the circulatory-system evaluation device of FIG. 1.

FIG. 2 shows a thoracic-cavity pressure applicator and measurement device 63. The pressure applicator and measurement device 63 includes a mouthpiece 66 that is connected to a pressure gauge 64 via a hollow rubber tube 65. The pressure gauge 64 is suitably a mercury pressure gauge.

When a circulatory-system evaluation measurement is initiated, the CPU 29 illuminates an indicator lamp 67. When the indicator lamp 67 is illuminated, the subject being evaluated executes the well-known Valsalva's operation. During the Valsalva's operation, the subject bites down on, and blows into, the mouthpiece 66. The subject blows into the mouthpiece with a force sufficient to maintain a predetermined pressure reading on the pressure gauge 64 for a predetermined period of time. As an example, the subject being evaluated blows into the mouthpiece 66 with a force sufficient to maintain a pressure value of approximately 40 mmHg for a period of approximately 15 seconds. After the predetermined period of time has expired, the subject removes the mouthpiece and resumes normal breathing.

During the predetermined period of time during which the subject is blowing into the mouthpiece 66, the pressure inside the subject's thoracic cavity is maintained at an elevated level, resulting in an increase in the subject's blood pressure from an initial level. When the subject resumes normal breathing after the predetermined of time has elapsed, the pressure inside the subject's thoracic cavity returns to normal levels and the subject's blood pressure decreases back to its initial level.

Figure 3:
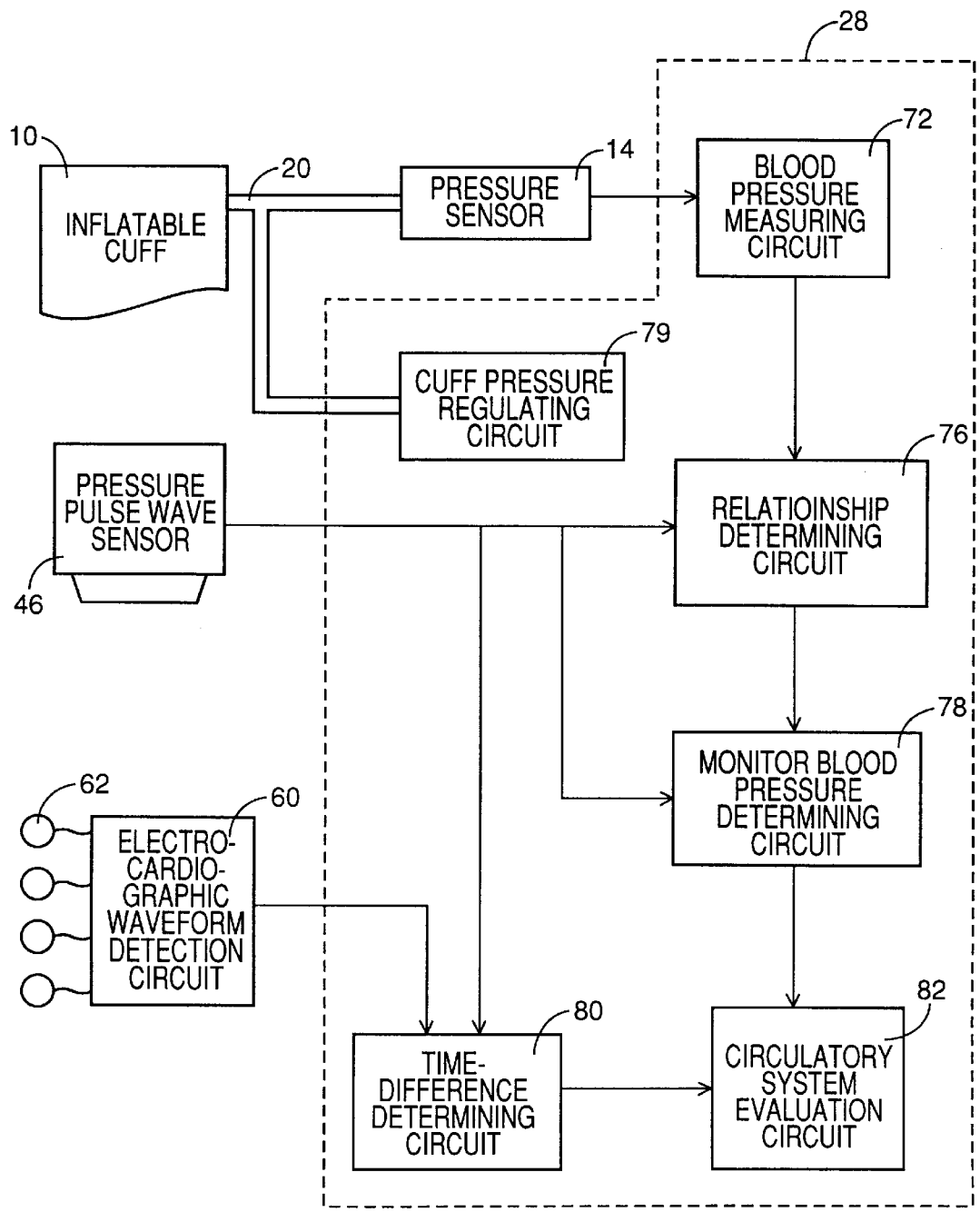
FIG. 3 is a block diagram of an electronic control device of the circulatory-system evaluation device of FIG. 1.

FIG. 3 illustrates the control functions of a first preferred embodiment of the electronic control device 28 of the circulatory-system evaluation device 8.

The electronic control device 28 regulates the air pressure in the inflatable cuff 10 via a cuff-pressure regulating circuit 79. When a circulatory system evaluation measurement is initiated, the cuff-pressure regulating circuit 79 switches the switch valve 16 to the inflation position and drives the first air pump 18 to quickly increase the air pressure in the inflatable cuff 10 to a predetermined target value, e.g., 180 mmHg. Subsequently, the cuff-pressure regulating circuit 79 switches the switch valve 16 to a slow-deflation position to slowly decrease the air pressure in the inflatable cuff 10.

While the air pressure in the inflatable cuff 10 is slowly decreasing, a blood-pressure measuring circuit 72 uses a well-known oscillometric method to measure the subject's systolic blood pressure, diastolic blood pressure and mean blood pressure. The blood pressure measurement is based on the variation in the amplitudes of the heartbeat-synchronous pulses of the oscillatory pressure-pulse waves (i.e., of the cuff oscillatory pressure-pulse-wave signal $SM_1$) obtained through the pressure-pulse-wave discrimination circuit 24 while the air pressure in the inflatable cuff 10 slowly decreases.

The pressure-pulse-wave sensor 46 is preferably pressed on the body surface 38 of the subject's wrist 42 on the subject's other arm from the arm 12 on which the inflatable cuff 10 is worn. The pressure-pulse-wave sensor 46 detects a oscillatory pressure-pulse wave produced from the radial artery 56 of the subject's wrist 42.

A relationship determining circuit 76 determines a relationship between a monitor-blood-pressure value MBP and a oscillatory pressure-pulse-wave magnitude $P_M$ based on at least one blood pressure value measured by the blood-pressure measuring circuit 72 and at least one oscillatory pressure-pulse wave (i.e., of the oscillatory pressure-pulse-wave signal $SM_2$) detected by the pressure-pulse-wave sensor 46. This relationship is determined for each subject and each circulatory evaluation measurement.

Figure 4:
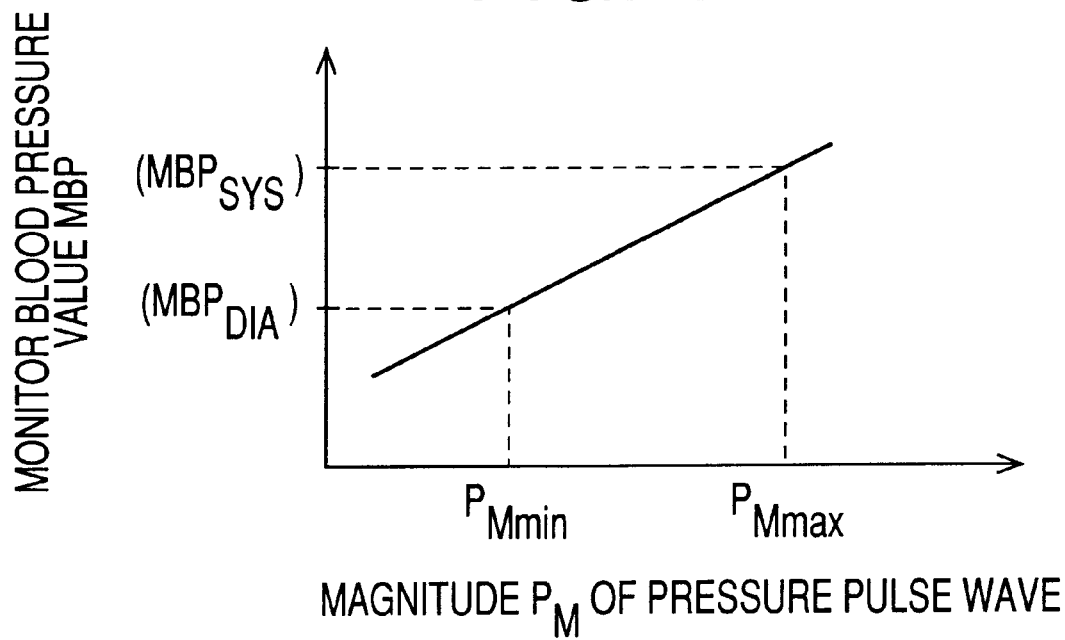
FIG. 4 shows a relationship between a subject's oscillatory pressure-pulse wave and a subject's blood pressure.

As shown in FIG. 4, this relationship may be one which is defined by the following linear function:

$$MBP = AP_M + B \tag{1}$$

where:

A is a constant representing the slope of the linear function; and

B is a constant representing an intercept of the linear function.

A monitor-blood-pressure determining circuit 78 successively determines, based on the relationship between the monitor-blood-pressure value MBP and the magnitude $P_M$ of the oscillatory pressure-pulse wave, a systolic monitor-blood-pressure value $MBP_{SYS}$ and a diastolic monitor-blood-pressure value $MBP_{DIA}$ based on the magnitudes $P_M$ of each heartbeat-synchronous pulse of the oscillatory pressure-pulse waves (i.e., of the oscillatory pressure-pulse-wave signal $SM_2$) detected by the pressure-pulse-wave sensor 46. Specifically, the maximum (upper-peak) magnitude $P_{Mmax}$ and minimum (lower-peak) magnitude $P_{Mmin}$ of each heartbeat-synchronous pulse is used to determine the systolic monitor-blood-pressure value $MBP_{SYS}$ and the diastolic monitor-blood-pressure value $MBP_{DIA}$. The monitor-blood-pressure values determined by the monitor-blood-pressure determining circuit 78 are continuously output to the display device 32. The display device 32 successively displays the determined monitor-blood-pressure values for each heartbeat-synchronous pulse.

Figure 5:
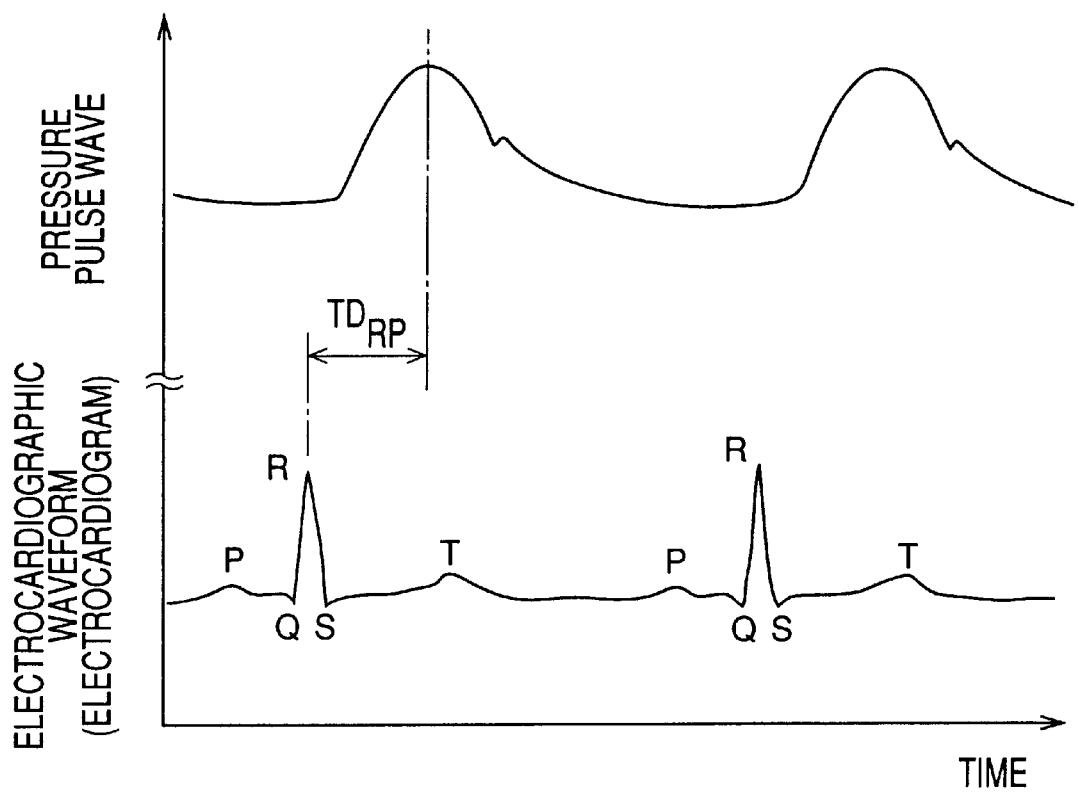
FIG. 5 is a timing chart of the circulatory-system evaluation device of FIG. 1.

After each systolic and diastolic monitor-blood-pressure value is determined by the monitor-blood-pressure determining circuit 78, a time-difference determining circuit 80 determines a time difference $TD_{RP}$ between a predetermined periodic point on the electrocardiographic waveform and a predetermined periodic point on a corresponding oscillatory pressure-pulse wave. In the preferred embodiments, the time-difference determining circuit 80 determines the time difference $TD_{RP}$ between an R point on the electrocardiographic waveform and a maximum point (upper-peak) of a pulse of a corresponding oscillatory pressure-pulse wave, as shown in FIG. 5. The time difference $TD_{RP}$ corresponds to the time it takes the oscillatory pressure-pulse wave to propagate from the aorta to the radial artery of the subject's arm.

A circulatory-system evaluation circuit 82 illuminates the indicator lamp 67 to initiate the Valsalva's operation, in which the subject blows into the mouthpiece 66 of the thoracic-cavity pressure applicator and measurement device 63.

The circulatory-system evaluation circuit 82 maintains the indicator lamp 67 in an illuminated state for a predetermined period of time, e.g., fifteen seconds. During this period of time, the subject continues to blow into the mouthpiece 66 with a force sufficient to maintain a predetermined pressure reading on the pressure gauge 64 of the pressure applicator and measurement device 63, e.g., 40 mmHg. The pressure indicated on the pressure gauge 64 corresponds to an internal pressure in the subject's thoracic cavity. The internal pressure generated in the subject's thoracic cavity causes a rise in the subject's blood pressure from an initial value.

After the predetermined period of time has elapsed, the circulatory-system evaluation circuit 82 turns off the indicator lamp 67. This signals the subject to remove the mouthpiece 66 and resume normal breathing. The resumption of normal breathing causes the subject's blood pressure to decrease back to its initial value.

While the subject's blood pressure is changing, the monitor-blood-pressure determining circuit 78 determines the monitor-blood-pressure values $MBP_{SYS}$ and $MBP_{DIA}$, and the time-difference determining circuit 80 determines corresponding time differences $TD_{RP}$.

While the subject's blood pressure is changing, the circulatory-system evaluation circuit 82 makes a curve of the relationship between changes in the monitor-blood-pressure values determined by the monitor-blood-pressure determining circuit 78, preferably the systolic monitor-blood-pressure values $MBP_{SYS}$, and corresponding changes in the time differences $TD_{RP}$ determined by the time-difference determining circuit 80, as shown in FIG. 6.

As shown in FIG. 6, time difference $TD_{RP}$ and the systolic monitor-blood-pressure value $MBP_{SYS}$ change linearly as the subject's blood pressure changes for a healthy subject, as shown by the line labeled "Healthy Subject." In contrast, as shown in FIG. 6, the time difference $TD_{RP}$ and the systolic monitor-blood-pressure value $MBP_{SYS}$, as the subject's blood pressure changes, varies over an elliptical path when the subject has a circulatory system ailment, such as, for example, arteriosclerosis. As shown in FIG. 6, the graph of $TD_{RP}$ vs. $MBP_{SYS}$ for a subject with a circulatory system ailment exhibits hysteresis. In other words, the time difference values determined by the time-difference determining circuit 80 as the subject's systolic monitor-blood-pressure value increases differ from the time difference values determined while the subject's systolic monitor-blood-pressure value decreases. In a healthy subject, as shown in FIG. 6, the graph of $TD_{RP}$ vs. $MBP_{SYS}$ does not exhibit hysteresis.

When the graph of $TD_{RP}$ vs. $MBP_{SYS}$ exhibits hysteresis, the circulatory-system evaluation circuit 82 determines the area enclosed by the ellipse-shaped curve. The circulatory-system evaluation circuit 82 then determines the degree of the circulatory ailment in the subject, e.g., the degree of arteriosclerosis, by comparing the area of the ellipse-shaped curve to predetermined standardized values.

Figure 7A:
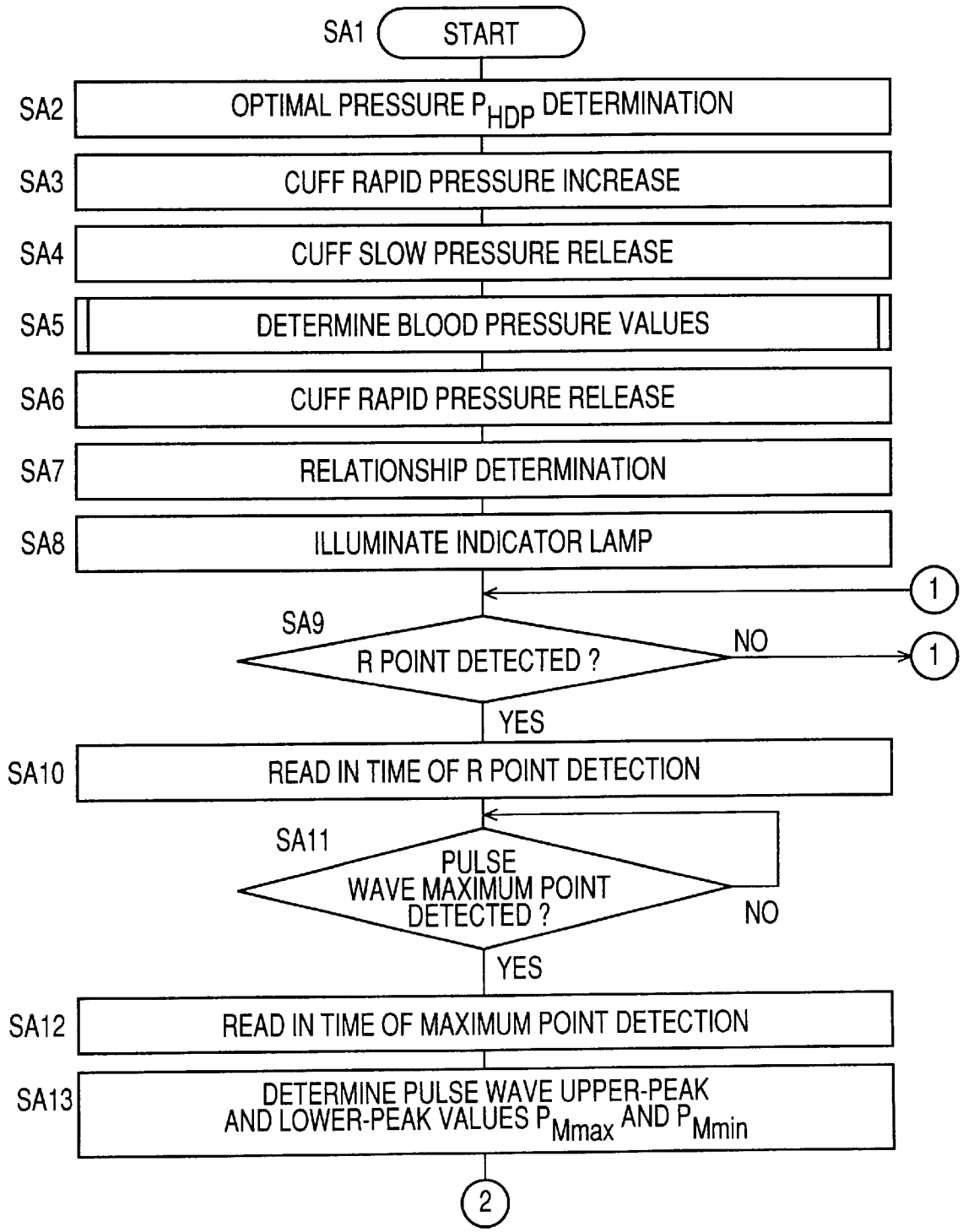
FIGS. 7A and 7B show a flowchart of a preferred control routine for the circulatory-system evaluation device of FIGS. 1 and 3.
Figure 7B:
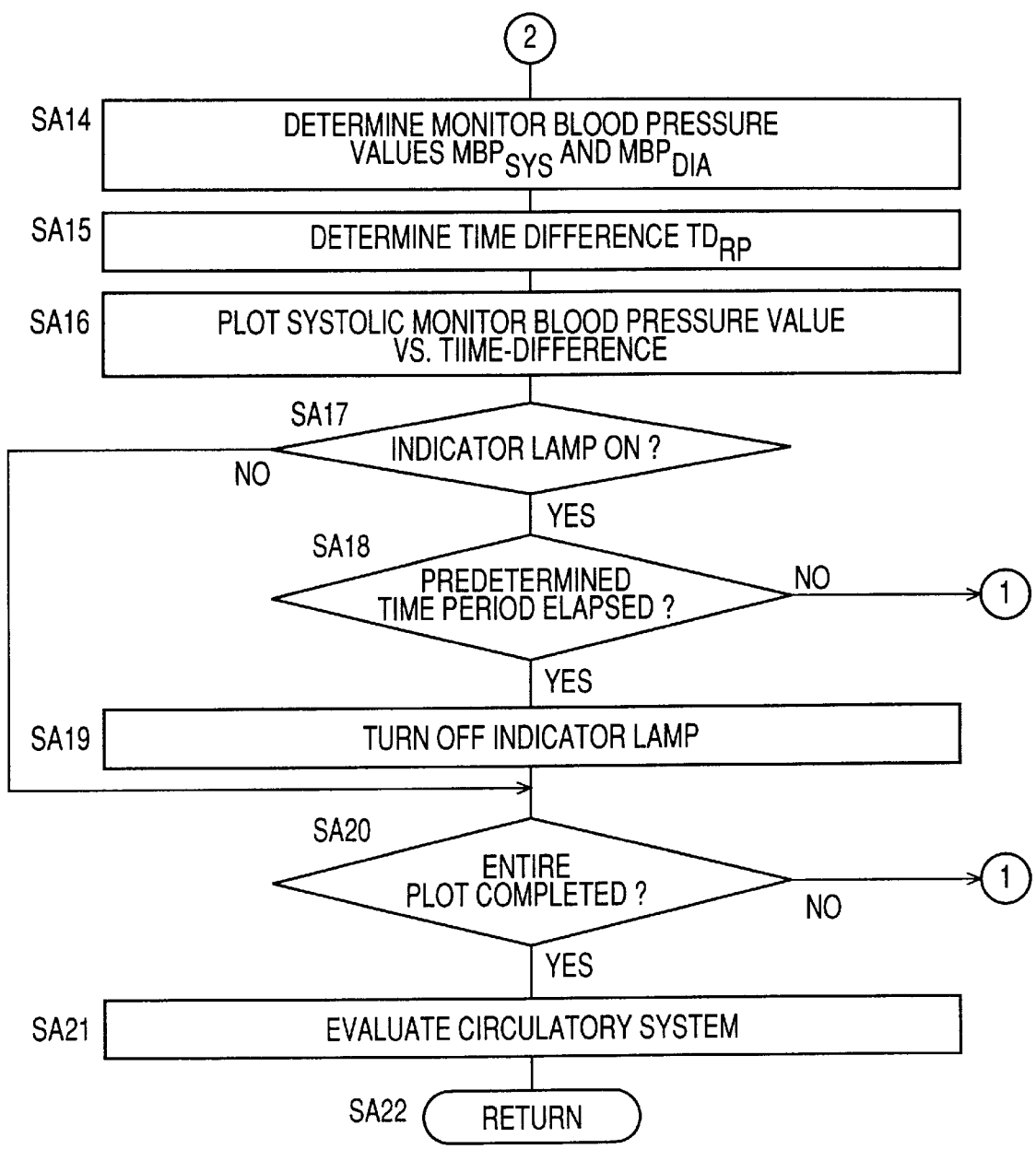

FIGS. 7A and 7B show a flowchart of a preferred control routine for the circulatory-system evaluation device 8 shown in FIG. 1 using the electronic control device of FIG. 3. The control routine starts at SA1 and proceeds to step SA2, where the control system controls the second air pump 50 and the pressure regulator valve 52 to vary the air pressure inside the pressure chamber 48. The control system gradually varies the pressure inside the pressure chamber 48 until the control system determines that the pressure inside the pressure chamber 48 maximizes the amplitude of the oscillatory pressure-pulse wave detected by the pressure-pulse-wave sensor 46. The pressure inside the chamber that maximizes the amplitude of the oscillatory pressure-pulse wave is the optimal pressure force $P_{HD}$ of the pressure-pulse-wave sensor 46. The control system then maintains this pressure during the course of the circulatory system evaluation measurement.

Control then continues to step SA3, where the control system increases the air pressure in the inflatable cuff 10 until a target pressure value is reached, e.g., 180 mmHg. The control system accomplishes this by switching the switch valve 16 to the inflation position and turning on the first air pump 18. When the air pressure in the inflatable cuff 10 reaches the target pressure value, the control system stops the first air pump 18. In step SA4, the control system switches the switch valve 16 to the slow-deflation position. Accordingly, the air pressure in the inflatable cuff 10 gradually decreases, preferably at a rate of 3 mmHg/sec.

Next, in step SA5, the blood-pressure measuring circuit 72 determines the subject's systolic, diastolic and mean blood pressure from the changes in the amplitudes in the cuff oscillatory pressure-pulse waves detected during the slow release of air from the inflatable cuff 10. As discussed above, the subject's blood pressure is determined using well-known oscillometric techniques. In addition, the blood-pressure measuring circuit 72 determines the subject's pulse rate from the time interval between the respective times of detection of two successive heartbeat-synchronous pulses of the cuff oscillatory pressure-pulse-wave signal. Control then continues to step SA6.

In step SA6, the control system switches the switch valve 16 to the quick-deflation position to rapidly release the remaining air in the inflatable cuff 10. In step SA7, the relationship determining circuit 76 determines a relationship between the blood pressure values determined at step SA5 and the magnitudes $P_{Mmax}$ and $P_{Mmin}$ of the oscillatory pressure-pulse waves detected by pressure-pulse-wave sensor 46.

Next, at step SA8, the control system illuminates the indicator lamp 67, which signals the subject to start the Valsalva's operation by blowing into the mouthpiece 66 of the thoracic-cavity pressure applicator and measurement device 63. In step SA9, the control system determines whether the R point on the electrocardiographic waveform has been detected. If the R point on the electrocardiographic waveform is detected, control continues to step SA10. Otherwise, control jumps back to step SA9.

In step SA10, the control system reads in the time at which the R point of the electrocardiographic waveform was detected. In step SA11, the control system determines if the maximum point of a corresponding oscillatory pressure-pulse wave detected by the pressure-pulse-wave sensor 46 has been detected. If the maximum point of the oscillatory pressure-pulse wave is detected, control continues to step SA12. Otherwise, control jumps back to step SA11.

In step SA12, the control system reads in the time at which the maximum point of the oscillatory pressure-pulse wave was detected. Next, at step SA13, the control system determines the oscillatory pressure-pulse wave upper-peak value $P_{Mmax}$ and the oscillatory pressure-pulse wave lower-peak value $P_{Mmin}$. Control then continues to step SA14.

In step SA14, the monitor-blood-pressure determining circuit 78 determines the systolic monitor-blood-pressure value $MBP_{SYS}$ and the diastolic monitor-blood-pressure value $MBP_{DIA}$ from the upper-peak and lower-peak values determined at step SA13 and the relationship determination made at step SA7. The control system then displays the determined monitor-blood-pressure values on the display device 32.

Next, at step SA15, the time-difference determining circuit 80 determines the time difference $TD_{RP}$ between the R point of the electrocardiographic waveform and the maximum point of the corresponding oscillatory pressure-pulse wave. Control then continues to step SA16.

In step SA16, the control system plots the time difference $TD_{RP}$ determined at step SA15 corresponding to the systolic monitor-blood-pressure value $MBP_{SYS}$ determined at step SA14. The resulting graph curve is preferably a two-dimensional curve, as shown in FIG. 6, with the systolic monitor-blood-pressure value $MBP_{SYS}$ plotted along one axis and the time difference $TD_{RP}$ plotted along an orthogonal axis.

Next, at step SA17, the control system determines if the indicator lamp 67 is still illuminated. If the indicator lamp 67 is illuminated, control continues to step SA18. Otherwise, control jumps to SA20.

In step SA18, the control system determines whether a predetermined time period has elapsed. The predetermined time period corresponds to a time period over which the Valsalva's operation is performed, e.g., fifteen seconds. If the predetermined time period has elapsed, control continues to step SA19. Otherwise, control returns to step SA9 and steps SA9–SA18 are repeated.

At step SA19, the control system turns off the indicator lamp 67. Then, at step SA20, the control system determines if an entire time difference versus systolic monitor blood pressure curve has been completed. In a preferred embodiment, the control system determines that the curve has been completed when it detects that a time difference/systolic monitor blood pressure data point has been repeated. If the entire curve has been completed, control continues to step SA21. Otherwise, control returns to SA9 and steps SA9–SA20 are repeated.

In step SA21, the circulatory-system evaluation circuit 82 determines the area enclosed by the time difference/systolic monitor blood pressure curve, as described above. The control system then displays the value of the area enclosed by the curve on the display device 32. Control then continues to step SA22, where the control routine stops.

Because the circulatory-system evaluation device 8 of this invention evaluates the circulatory system of a subject based on the relationship between changes in the time difference $TD_{RP}$ and changes in the subject's systolic monitor blood pressure $MBP_{SYS}$, it is possible to evaluate the improvement in a circulatory system disease brought about by dietary treatments and the like, even in subjects that are taking blood pressure reducing medication.

In addition, because the circulatory-system evaluation circuit 82 compares the area enclosed by the time difference/systolic monitor blood pressure curve to predetermined standardized values, a subject's circulatory system is quantitatively evaluated.

Furthermore, using a thoracic-cavity pressure applicator and measurement device 63, which assists the subject in maintaining a constant internal thoracic cavity pressure during the circulatory system evaluation measurement, improves the accuracy of the circulatory system evaluation.

In addition, because a common pressure-pulse-wave sensor 46 is used to determine the maximum point of the oscillatory pressure-pulse wave at step SA11 and the upper-peak and lower-peak values of the oscillatory pressure-pulse wave at step SA13, the cost of the circulatory-system evaluation device is reduced.

Figure 8:
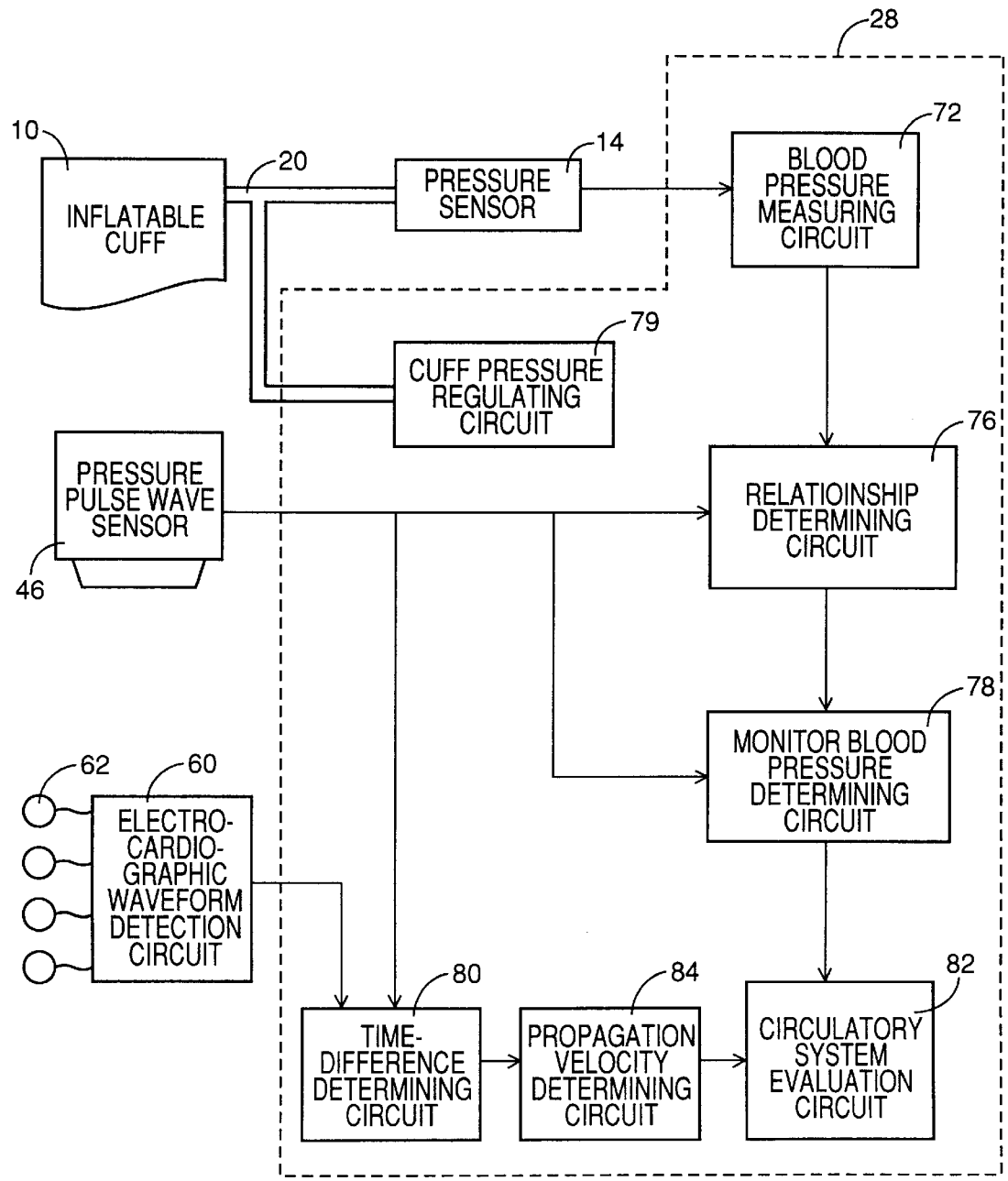
FIG. 8 is a block diagram of a second preferred embodiment of an electronic control device of the circulatory-system evaluation device of FIG. 1.

FIG. 8 is a second embodiment of the electronic control device 28 of the circulatory-system evaluation device 8. The embodiment of FIG. 8 includes a propagation velocity determining circuit 84. Otherwise, the embodiment of FIG. 8 is identical to the embodiment shown in FIG. 3. Accordingly, common elements are labeled with the same element numbers.

In the embodiment shown in FIG. 8, the propagation velocity determining circuit 84 determines a propagation rate $V_M$ (m/sec) of the oscillatory pressure-pulse wave. The oscillatory pressure-pulse wave propagates through an artery of the subject, including the radial artery of the subject's right arm 12. The propagation velocity determining circuit 84 calculates the propagation velocity $V_M$ based on the time difference $TD_{RP}$ determined by the time-difference determining circuit 80 according to the formula:

$$V_M = L/(TD_{RP} - T_{PEP}) \quad (2)$$

where:

L is the length in meters of the subject's artery from the left ventricle to the point where the pressure-pulse-wave sensor 46 presses against the radial artery, including the lengths of the aorta, the brachial artery and the radial artery; and $T_{PEP}$ is the pre-ejection period between a Q point of the electrocardiographic waveform and a minimum point (i.e., rising point) of an aortic pulse wave waveform. The values L and $T_{PEP}$ in Equation (2) are experimentally determined in advance. Equation (2) is preferably pre-stored in the ROM 31.

Figure 9A:
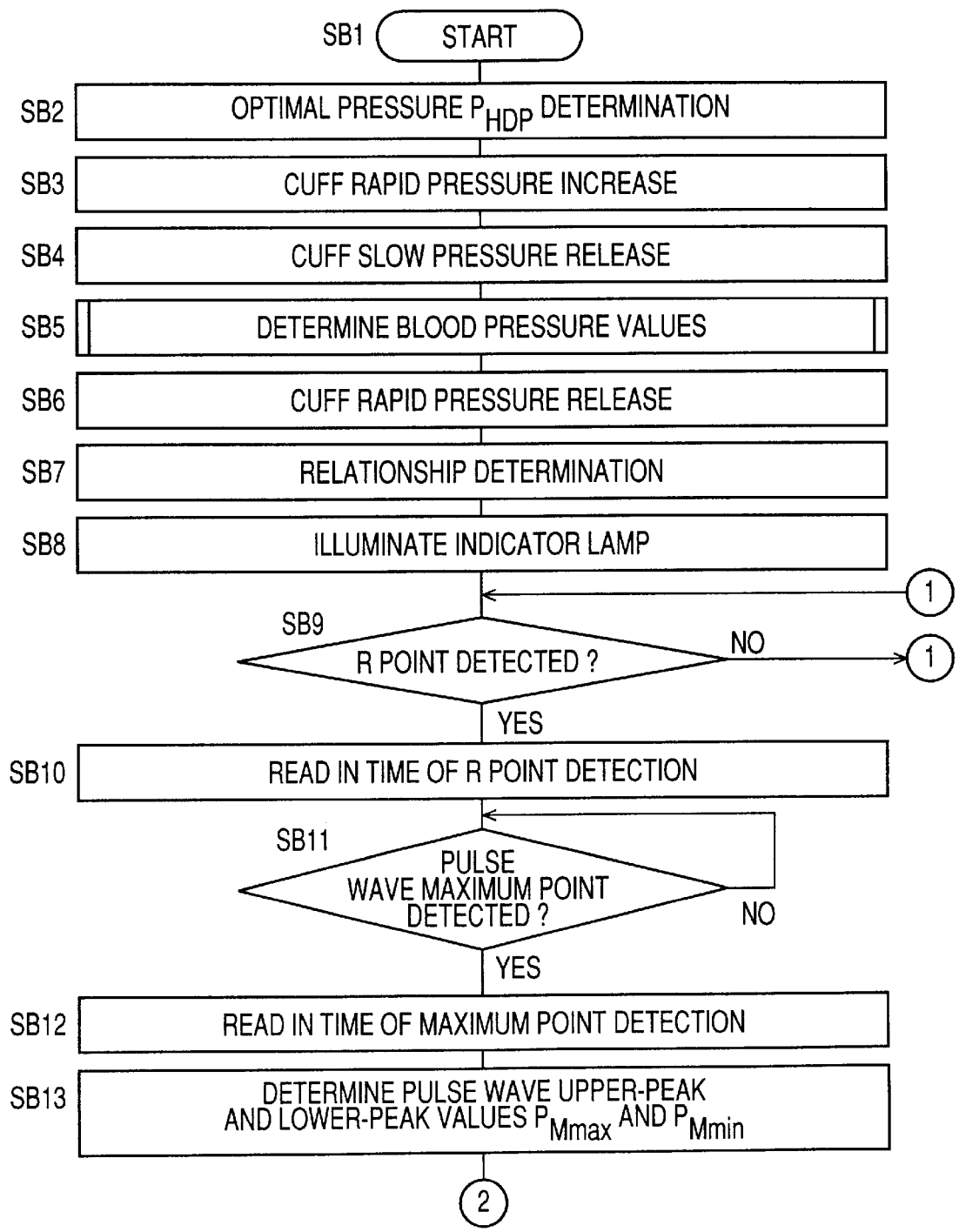
FIGS. 9A and 9B show a flowchart of a preferred control routine for the circulatory-system evaluation device of FIGS. 1 and 8.
Figure 9B:
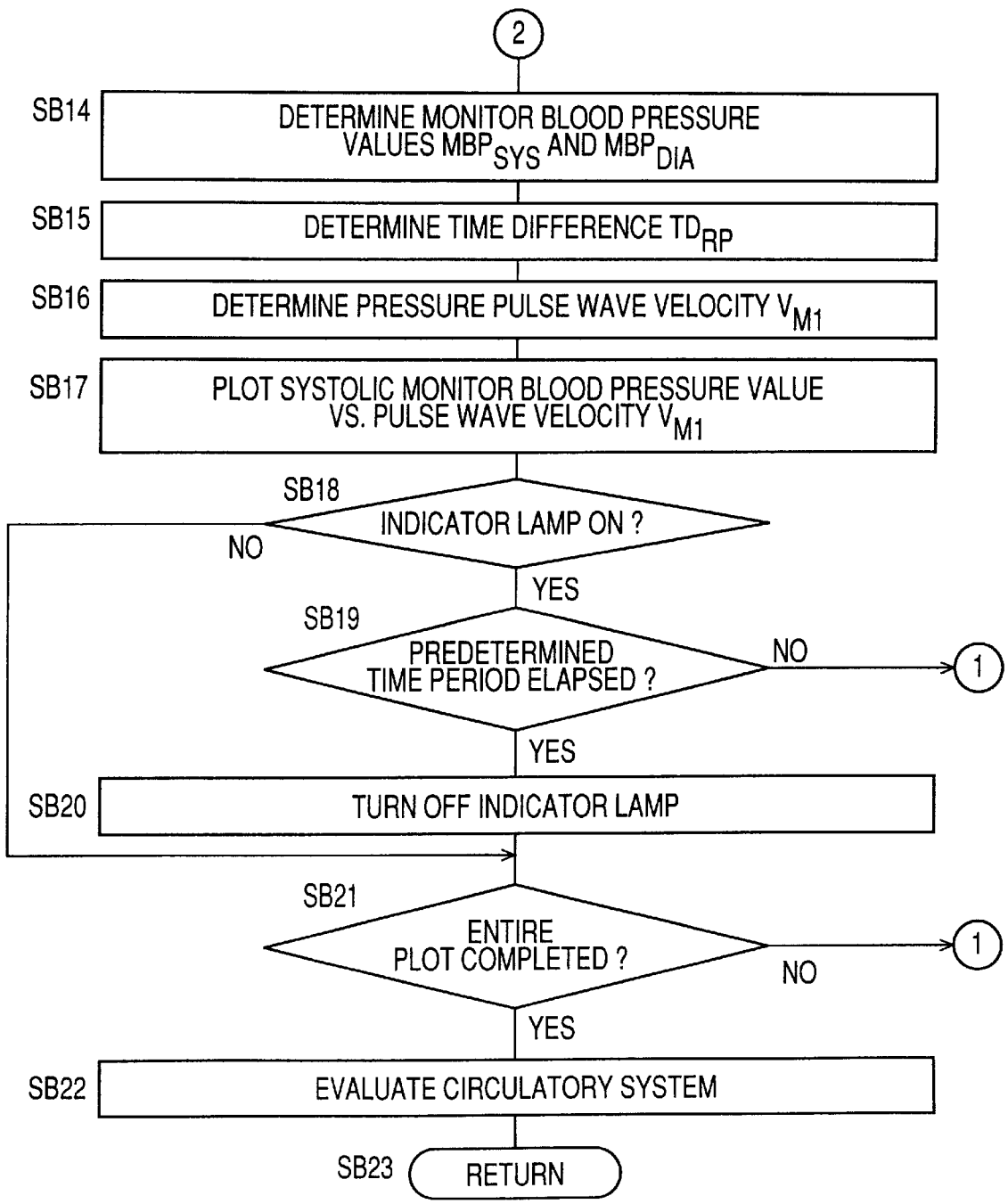

FIGS. 9A and 9B show a flowchart of a preferred control routine for the circulatory-system evaluation device of FIG. 1 using the electronic control device 28 shown in FIG. 8. The routine starts at SB1 and proceeds to step SB2, where the control system controls the second air pump 50 and the pressure regulator valve 52 to vary the air pressure inside the pressure chamber 48. The control system gradually varies the pressure inside the pressure chamber 48 until the control system determines that the pressure inside the pressure chamber 48 maximizes the amplitude of the oscillatory pressure-pulse wave detected by the pressure-pulse-wave sensor 46. The pressure inside the chamber that maximizes the amplitude of the oscillatory pressure-pulse wave is the optimal pressure force $P_{HD}$ of the pressure-pulse-wave sensor 46. The control system then maintains this pressure during the course of the circulatory system evaluation measurement.

Control then continues to step SB3, where the control system increases the air pressure in the inflatable cuff 10 until a target pressure value is reached, e.g., 180 mmHg. The control system accomplishes this by switching the switch valve 16 to the inflation position and turning on the first air pump 18. When the air pressure in the inflatable cuff 10 reaches the target pressure value, the control system stops the first air pump 18. In step SB4, the control system switches the switch valve 16 to the slow-deflation position. Accordingly, the air pressure in the inflatable cuff 10 gradually decreases, preferably at a rate of 3 mmHg/sec.

Next, in step SB5, the blood-pressure measuring circuit 72 determines the subject's systolic, diastolic and mean blood pressure from the changes in the amplitudes in the cuff oscillatory pressure-pulse waves detected during the slow release of air from the inflatable cuff 10. As discussed above, the subject's blood pressure is determined using well-known oscillometric techniques. In addition, the blood-pressure measuring circuit 72 determines the subject's pulse rate from the time interval between the respective times of detection of two successive heartbeat-synchronous pulses of the cuff oscillatory pressure-pulse-wave signal. Control then continues to step SB6.

In step SB6, the control system switches the switch valve 16 to the quick-deflation position to rapidly release the remaining air in the inflatable cuff 10. In step SB7, the relationship determining circuit 76 determines a relationship between the blood pressure values determined at SB5 and the magnitudes $P_{Mmax}$ and $P_{Mmin}$ of the oscillatory pressure-pulse waves detected by pressure-pulse-wave sensor 46.

Next, at step SB8, the control system illuminates the indicator lamp 67, which signals the subject to start the Valsalva's operation by blowing into the mouthpiece 66 of the thoracic-cavity pressure applicator and measurement device 63. In step SB9, the control system determines whether the R point on the electrocardiographic waveform has been detected. If the R point on the electrocardiographic waveform is detected, control continues to step SB10. Otherwise, control jumps back to step SB9.

In step SB10, the control system reads in the time at which the R point of the electrocardiographic waveform was detected. In step SB11, the control system determines if the maximum point of a corresponding oscillatory pressure-pulse wave detected by the pressure-pulse-wave sensor 46 has been detected. If the maximum point of the oscillatory pressure-pulse wave is detected, control continues to step SB12. Otherwise, control jumps back to step SB11.

In step SB12, the control system reads in the time at which the maximum point of the oscillatory pressure-pulse wave was detected. Next, at step SB13, the control system determines the oscillatory pressure-pulse wave upper-peak value $P_{Mmax}$ and the oscillatory pressure-pulse wave lower-peak value $P_{Mmin}$. Control then continues to step SB14.

In step SB14, the monitor-blood-pressure determining circuit 78 determines the systolic monitor-blood-pressure value $MBP_{SYS}$ and the diastolic monitor-blood-pressure value $MBP_{DIA}$ from the upper-peak and lower-peak values determined at step SB13 and the relationship determination made at step SB7. The control system then displays the determined monitor-blood-pressure values on the display device 32.

Next, at step SB15, the time-difference determining circuit 80 determines the time difference $TD_{RP}$ between the R point of the electrocardiographic waveform and the maximum point of the corresponding oscillatory pressure-pulse wave. Control then continues to step SA16.

In step SB16, the control system determines the propagation velocity $V_{M1}$ of the oscillatory pressure-pulse wave based on the time difference $TD_{RP}$ determined at step SB15.

Next, in step SB17, the control system plots the propagation velocity $V_{M1}$ determined at step SB16 corresponding to the systolic monitor-blood-pressure value $MBP_{SYS}$ determined at step SB14. The resulting graph is preferably a two-dimensional curve, as shown in FIG. 10, with the systolic monitor-blood-pressure value $MBP_{SYS}$ plotted along one axis and the pressure-pulse wave propagation velocity $V_{M1}$ plotted along an orthogonal axis.

Next, at step SB18, the control system determines if the indicator lamp 67 is still illuminated. If the indicator lamp 67 is illuminated, control continues to step SB19. Otherwise, control jumps to SB21.

In step SB19, the control system determines whether a predetermined time period has elapsed. The predetermined time period corresponds to a time period over which the Valsalva's operation is performed, e.g., fifteen seconds. If the predetermined time period has elapsed, control continues to step SB20. Otherwise, control returns to step SB9 and steps SB9–SB19 are repeated.

At step SB20, the control system turns off the indicator lamp 67. Then, at step SB21, the control system determines if an entire propagation velocity versus systolic monitor blood pressure curve has been completed. In a preferred embodiment, the control system determines that the curve has been completed when it detects that a propagation velocity/systolic monitor blood pressure data point has been repeated. If the entire curve has been completed, control continues to step SB22. Otherwise, control returns to SB9 and steps SB9–SB21 are repeated.

In step SB22, the circulatory-system evaluation circuit 82 determines the area enclosed by the propagation velocity/systolic monitor blood pressure curve, as described above. The control system then displays the value of the area enclosed by the curve on the display device 32. Control then continues to step SB22, where the control routine stops.

The electronic control device 28, including the blood-pressure measuring circuit 72, the cuff regulating circuit 79, the relationship determining circuit 76, the monitor-blood-pressure determining circuit 78, the time-difference determining circuit 80 and the circulatory-system evaluation circuit 82, and optionally the propagation velocity determining circuit 84, is preferably implemented using a programmed general purpose computer. However, the electronic control device can also be implemented using a special purpose computer, a programmed microprocessor or microcontroller and peripheral integrated circuit elements, an ASIC or other integrated circuit, a hardwired electronic or logic circuit such as a discrete element circuit, a programmable logic device such as a FPGA, a PLD, a PLA or a PAL, or the like. In general, any device on which a finite state machine capable of implementing the flowcharts shown in FIGS. 7A and 7B or FIGS. 9A and 9B and capable of controlling the peripheral devices shown in FIGS. 3 and 8 can be implemented, can be used to implement the electronic control device 28 of this invention.

While this invention has been described in conjunction with the specific embodiments outlined above, it is evident that many alternatives, modifications and variations will be apparent to those skilled in the art. For example, although the circulatory-system evaluation circuit 82 utilizes the time difference $TD_{RP}$ between the R point of the electrocardiographic waveform and the maximum point of the oscillatory pressure-pulse wave, it may also utilize a time difference $TD_{QP}$ between a Q point of the electrocardiographic waveform and a maximum point of the oscillatory pressure-pulse wave. In addition, the time difference may be defined from an S point of the electrocardiographic waveform to the maximum point of the oscillatory pressure-pulse wave. Furthermore, the time difference may be defined from an R point, a Q point or an S point to a minimum point of the oscillatory pressure-pulse wave.

In addition, in the embodiments described above, the areas enclosed by the time difference/systolic monitor-blood-pressure value curve and the propagation velocity/systolic monitor blood pressure curve are displayed as numerical values on the display device 32. However, the curves themselves may be graphically displayed on the display device 32 in addition to or instead of the numerical values of the areas.

Furthermore, although a mercury pressure gauge is preferably used for the pressure gauge 64 of the thoracic-cavity pressure applicator and measurement device 63, an aneroid or other type of pressure gauge may be used.

Additionally, although the control system signals a subject to begin the Valsalva's operation by illuminating the indicator lamp 67, the control system may also use other means to signal the subject. For example, the control system can sound a buzzer to signal the subject.

Furthermore, although the circulatory-system evaluation circuit 82 preferably graphs the time difference $TD_{RP}$ or the propagation velocity $V_{M1}$ as a function of the systolic monitor-blood-pressure value $MBP_{SYS}$, the circulatory-system evaluation circuit 82 may also evaluate a subject's circulatory system by curveting the time difference $TD_{RP}$ or the propagation velocity $V_{M1}$ as a function of the diastolic monitor-blood-pressure value $MBP_{DIA}$.

In addition, although the preferred embodiment utilizes a Valsalva's operation to change the subject's blood pressure during the circulatory system evaluation measurement, other means of changing the subject's blood pressure may be utilized. For example, a treadmill may be used to change the subject's blood pressure by having the subject run on a treadmill for a predetermined period of time.

In the second embodiment described above, the propagation velocity $V_{M1}$ is determined based on the time difference $TD_{RP}$ between each pulse of the electrocardiographic waveform and a corresponding pulse of the oscillatory pressure-pulse wave. However, the propagation velocity may be determined based on a time difference between a heartbeat-synchronous pulse of a first oscillatory pressure-pulse wave detected by the pressure sensor 14 and a corresponding heartbeat-synchronous pulse of a second oscillatory pressure-pulse wave detected by the pressure-pulse-wave sensor 46.

Furthermore, the propagation velocity $V_{M1}$ of the oscillatory pressure-pulse wave may be measured by attaching a set of pressure-pulse-wave sensors to the carotid and the femoral arteries of the subject.

Accordingly, the preferred embodiments of the invention as set forth above are intended to be illustrative, not limiting. Various changes may be made without departing from the spirit and scope of the invention as defined in the following claims.

What is claimed is:

1. A device for evaluating a circulatory system of a living subject, comprising:
   a blood-pressure changing device that changes a blood pressure of the living subject;
   a blood-pressure measuring device that measures the blood pressure of the living subject while the living subject's blood pressure is changing;
   an oscillatory pressure-pulse wave detector that detects oscillatory pressure-pulse waves of the living subject while the living subject's blood pressure is changing, the oscillatory pressure-pulse waves produced by a cardiac muscle of the living subject propagating along an artery of the living subject;
   an electrocardiographic waveform detector that detects an electrocardiographic waveform of the living subject;
   a time-difference determining circuit that determines time differences between predetermined periodic points on the electrocardiographic waveform of the living subject and predetermined periodic points on corresponding oscillatory pressure-pulse waves of the living subject; and
   a circulatory-system evaluation circuit that evaluates the living subject's circulatory system based on a relationship between changes in the living subject's blood pressure and changes in the corresponding time differences determined by the time-difference determining circuit.

2. The device of claim 1, wherein the blood-pressure changing device comprises a strain application device that applies a strain to the living subject for a predetermined period of time, the subject's blood pressure increasing from an initial value in response to the strain and decreasing back to the initial value when the strain is removed.

3. The device of claim 2, wherein the strain application device comprises:
   a pressure gauge that measures an air pressure;
   a mouthpiece; and
   a hollow tube connecting the mouthpiece to the pressure gauge, wherein the living subject begins a strain operation by blowing into the mouthpiece with a force sufficient to register a predetermined air pressure value on the pressure gauge.

4. The device of claim 3, wherein the pressure gauge comprises a mercury pressure gauge.

5. The device of claim 2, further comprising a signaling device that signals the living subject to begin a strain operation with the strain application device.

6. The device of claim 5, wherein the signaling device comprises a lamp.

7. The device of claim 1, wherein the blood-pressure measuring device comprises:
   a blood-pressure measuring circuit that determines a systolic blood pressure and a diastolic blood pressure of the living subject;
   a relationship determining circuit that determines a first relationship between the blood pressure values determined by the blood-pressure measuring circuit and magnitudes of corresponding oscillatory pressure-pulse waves detected by the oscillatory pressure-pulse-wave detector; and
   a monitor-blood-pressure determining circuit that determines monitor-blood-pressure values based on the first relationship determined by the relationship determining circuit and magnitudes of the oscillatory pressure-pulse wave.

8. The device of claim 7, wherein the monitor-blood-pressure determining circuit determines systolic monitor-blood-pressure values and diastolic monitor-blood-pressure values.

9. The device of claim 7, wherein the circulatory-system evaluation circuit determines a second relationship between the monitor-blood-pressure values determined by the monitor-blood-pressure determining circuit and corresponding time differences determined by the time-difference determining circuit.

10. The device of claim 9, wherein the circulatory-system evaluation circuit evaluates the living subject's circulatory system based on an amount of hysteresis present in the second relationship.

11. The device of claim 1, wherein the oscillatory pressure-pulse wave detector comprises:
   a housing having an opening;
   a diaphragm attached to the housing;
   a sensor capable of sensing the oscillatory pressure-pulse wave and supported by the diaphragm so that the sensor is movable relative to the housing and is advanceable through the opening of the housing; and
   an attachment mechanism capable of attaching the oscillatory pressure-pulse wave detector to a portion of the living subject;
   the housing, the diaphragm and the sensor defining a pressure chamber capable of receiving pressurized air, the pressurized air applying a pressing force to the sensor to press the sensor against the living subject when the oscillatory pressure-pulse wave detector is attached to the living subject.

12. The device of claim 1, wherein the electrocardiographic waveform detector comprises:
   a plurality of electrocardio electrodes, the electrocardio electrodes capable of sensing an electrocardiographic signal from the living subject when the electrocardio electrodes are in electrical contact with the living subject; and
   an electrocardiographic-waveform detection circuit that detects the living subject's electrocardiographic waveform based on the electrocardiographic signals sensed by the electrocardio electrodes.

13. A device for evaluating a circulatory system of a living subject, comprising:
   a blood-pressure changing device that changes a blood pressure of the living subject;
   a blood-pressure measuring device that measures the blood pressure of the living subject while the living subject's blood pressure is changing;

an electrocardiographic waveform detector that detects an electrocardiographic waveform of the living subject;

an oscillatory pressure-pulse wave detector that detects oscillatory pressure-pulse waves of the living subject while the living subject's blood pressure is changing, that oscillatory pressure-pulse wave produced by a cardiac muscle of the living subject and propagating along an artery of the living subject;

an oscillatory pressure-pulse wave velocity determining device that determines propagation velocities of the oscillatory pressure-pulse waves; and a circulatory-system evaluation circuit that evaluates the living subject's circulatory system based on a relationship between changes in the living subject's blood pressure and changes in the propagation velocities of corresponding oscillatory pressure-pulse waves.

14. The device of claim 13, wherein the blood-pressure changing device comprises a strain application device that applies a strain to the living subject for a predetermined period of time, the subject's blood pressure increasing from an initial value in response to the strain and decreasing back to the initial value when the strain is removed.

15. The device of claim 14, wherein the strain application device comprises:

a pressure gauge that measures an air pressure;

a mouthpiece; and a hollow tube connecting the mouthpiece to the pressure gauge, wherein the living subject begins a strain operation by blowing into the mouthpiece with a force sufficient to register a predetermined air pressure value on the pressure gauge.

16. The device of claim 15, wherein the pressure gauge comprises a mercury pressure gauge.

17. The device of claim 14, further comprising a signaling device that signals the living subject to begin a strain operation with the strain application device.

18. The device of claim 17, wherein the signaling device comprises a lamp.

19. The device of claim 13, wherein the blood-pressure measuring device comprises:

a blood-pressure measuring circuit that determines a systolic blood pressure and a diastolic blood pressure of the living subject;

a relationship determining circuit that determines a first relationship between the blood pressure values determined by the blood-pressure measuring circuit and magnitudes of corresponding oscillatory pressure-pulse waves detected by the oscillatory pressure-pulse wave detector; and a monitor-blood-pressure determining circuit that determines monitor-blood-pressure values based on the first relationship determined by the relationship determining circuit and magnitudes of the oscillatory pressure waves.

20. The device of claim 19, wherein the monitor-blood-pressure determining circuit determines systolic monitor-blood-pressure values and diastolic monitor-blood-pressure values.

21. The device of claim 19, wherein the circulatory-system evaluation circuit determines a second relationship between the monitor-blood-pressure values determined by the monitor-blood-pressure determining circuit and propagation velocities of corresponding oscillatory pressure-pulse waves determined by the oscillatory pressure-pulse wave velocity determining device.

22. The device of claim 21, wherein the circulatory-system evaluation circuit evaluates the living subject's circulatory system based on an amount of hysteresis present in the second relationship.

23. The device of claim 13, wherein the oscillatory pressure-pulse wave detector comprises:

a housing having an opening;

a diaphragm attached to the housing;

a sensor capable of sensing the pressure-pulse-wave and supported by the diaphragm so that the sensor is movable relative to the housing and is advanceable through the opening of the housing; and an attachment mechanism capable of attaching the oscillatory pressure-pulse wave detector to a portion of the living subject;

the housing, the diaphragm and the sensor defining a pressure chamber capable of receiving pressurized air, the pressurized air applying a pressing force to the sensor to press the sensor against the living subject when the oscillatory pressure-pulse wave detector is attached to the living subject.

24. The device of claim 13, wherein the oscillatory pressure-pulse wave velocity determining device comprises:

a time-difference determining device that determines time differences between predetermined periodic points on the electrocardiographic waveform of the living subject and predetermined periodic points on the oscillatory pressure-pulse waves of the living subject; and a oscillatory pressure-pulse wave velocity determining circuit that determines a propagation velocity of the oscillatory pressure-pulse waves based on the time differences determined by the time-difference determining device.

25. The device of claim 24, wherein the electrocardiographic waveform detector comprises:

a plurality of electrocardio electrodes, the electrocardio electrodes capable of sensing an electrocardiographic signal from the living subject when the electrocardio electrodes are in electrical contact with the living subject; and an electrocardiographic-waveform detection circuit that detects the living subject's electrocardiographic waveform based on the electrocardiographic signals sensed by the electrocardio electrodes.

26. A device for evaluating a circulatory system of a living subject, comprising:

a blood-pressure measuring device that successively measures the blood pressure of the living subject while the living subject is subjected to a physical load;

a means for creating the physical load;

a pressure-pulse wave propagation velocity information obtaining device that, while the living subject is subjected to the physical load, successively obtains pressure-pulse wave propagation velocity information relating to a propagation velocity of a pressure-pulse wave through an artery of the living subject; and a circulatory-system evaluation circuit that evaluates the circulatory system of the living subject based on a relationship between changes in the blood pressure of the living subject and changes in the pressure-pulse wave propagation velocity information.

27. The device of claim 26, wherein the pressure-pulse wave propagation velocity information obtaining device comprises:

a first pulse wave detection circuit that detects first pulse waves from a first portion of the subject;

a second pulse wave detection circuit that detects second pulse waves from a second portion of the subject; and a time-difference determining circuit that determines, as the pressure-pulse wave propagation velocity information, time differences between predetermined periodic points on the first pulse waves and predetermined periodic points on the corresponding second pulse waves.

28. The device of claim 27, wherein the circulatory-system evaluation circuit comprises evaluating means for evaluating the circulatory system of the subject based on a relationship between changes in the blood pressure of the subject and changes in the time differences determined by the time-difference determining circuit.

29. The device of claim 28, wherein the pressure-pulse wave propagation velocity information obtaining device further comprises a propagation-velocity determining circuit that determines the propagation velocity of the pulse wave based on each of the time differences determined by the time-difference determining circuit, and wherein the circulatory-system evaluation circuit comprises evaluating means for evaluating the circulatory system of the subject based on a relationship between changes in the blood pressure of the subject and changes in the propagation velocities determined by the propagation-velocity determining circuit.

30. The device of claim 26, wherein the circulatory-system evaluation circuit comprises hysteresis determining means for determining an amount of hysteresis present in the relationship between the changes in the blood pressure of the subject and the changes in the pressure-pulse wave propagation velocity information.

31. The device of claim 30, wherein the hysteresis determining means comprises area-calculating means for calculating, as the amount of hysteresis, an area defined by a closed line representing the relationship between the changes in the blood pressure of the subject and the changes in the pressure-pulse wave propagation velocity information.

32. A method of evaluating a circulatory system of a living subject, comprising:

changing a blood pressure of the living subject over a predetermined period of time;

measuring the subject's blood pressure while the subject's blood pressure is changing;

measuring oscillatory pressure-pulse waves of the living subject while the living subject's blood pressure is changing, the oscillatory pressure-pulse waves produced by a cardiac muscle of the living subject and propagating along an artery of the living subject;

measuring an electrocardiographic waveform of the living subject while the living subject's blood pressure is changing;

determining time differences between predetermined periodic points on the electrocardiographic waveform of the living subject and predetermined periodic points on corresponding oscillatory pressure-pulse waves of the living subject; and evaluating the living subject's circulatory system based on a relationship between changes in the living subject's blood pressure and changes in corresponding time differences.

33. The method of claim 32, changing the blood pressure of the living subject comprises:

applying a strain on the living subject for a predetermined period of time to raise a blood pressure of the living subject from an initial value; and removing the strain applied to the living subject to lower the subject's blood pressure back to the initial value.

34. The method of claim 33, wherein applying a strain on the living subject comprises causing the living subject to blow into a mouthpiece of an air pressure gauge with a predetermined force for a predetermined period of time.

35. The method of claim 32, wherein measuring the subject's blood pressure comprises:

determining a systolic blood pressure value of the subject and a diastolic blood pressure value of the subject;

determining a first relationship between the blood pressure values and magnitudes of corresponding oscillatory pressure-pulse waves; and determining systolic and diastolic monitor-blood-pressure values based on the first relationship.

36. The method of claim 35, wherein evaluating the living subject's circulatory system comprises determining a second relationship between the monitor-blood-pressure values and corresponding time differences between predetermined periodic points on the electrocardiographic waveform of the living subject and predetermined periodic points on corresponding oscillatory pressure-pulse waves of the living subject.

37. The method of claim 36, wherein the subject's circulatory system is evaluated based on an amount of hysteresis present in the second relationship.

38. The method of claim 35, wherein propagation velocities of the oscillatory pressure-pulse waves are determined based on the time differences between predetermined periodic points on the electrocardiographic waveform of the living subject and predetermined periodic points on the oscillatory pressure-pulse waves of the living subject.

39. The method of claim 35, evaluating the living subject's circulatory system comprises determining a second relationship between the monitor-blood-pressure values and the propagation velocities of corresponding oscillatory pressure-pulse waves.

40. The method of claim 39, wherein the subject's circulatory system is evaluated based on an amount of hysteresis present in the second relationship.

* * * * *